United States Patent [19]

Cahiez et al.

[11] Patent Number: 5,110,962

[45] Date of Patent: May 5, 1992

[54] PREPARATION AND APPLICATION OF BROMINATED COMPOUNDS OF MANGANESE

[75] Inventors: Gérard Cahiez; Blandine Laboue, both of Paris; Pierre Tozzolino, Morlaas, all of France

[73] Assignee: Societe Nationale Elf Aquitaine, France

[21] Appl. No.: 566,331

[22] PCT Filed: Dec. 16, 1988

[86] PCT No.: PCT/FR88/00619

§ 371 Date: Aug. 15, 1990

§ 102(e) Date: Aug. 15, 1990

[51] Int. Cl.[5] .................. C07F 13/00; C07C 45/00
[52] U.S. Cl. .................... 556/46; 260/665 R; 568/383; 568/407; 568/409; 423/49; 423/499
[58] Field of Search ............ 556/46; 260/665 R; 568/383, 407, 409; 423/499, 49

[56] References Cited

U.S. PATENT DOCUMENTS 4,827,044  5/1989  Tozzolino et al. ................. 568/319

FOREIGN PATENT DOCUMENTS 0373050  6/1990  European Pat. Off. ............ 568/407

OTHER PUBLICATIONS

Cahiez et al., Tetrahedron Letters, vol. 26, No. 37, pp. 4441-4448, issued 1986.
G. Friour et al., Synthesis, vol. 1, pp. 37-40 (1984).
G. Friour et al., Tetrahedron, vol. 40, No. 4, pp. 683-693 (1984).
G. Cahiez et al., Tetrahedron Letters, No. 38, pp. 3383-3384 (1977).

Primary Examiner—Jose G. Dees
Assistant Examiner—Porfirio Nazario
Attorney, Agent, or Firm—Ostrolenk, Faber, Gerb & Soffen

[57] ABSTRACT

Manganese bromide solution for use in the formation of organomanganese compounds, applicable to the synthesis of organic products, particularly ketones.

16 Claims, No Drawings

PREPARATION AND APPLICATION OF BROMINATED COMPOUNDS OF MANGANESE

The invention relates to the preparation of brominated organomanganese compounds, as well as their application to the synthesis of organic compounds particularly ketones.

Recent developments in the chemistry of manganese halides, regarding the formation of organomanganase compounds, have mainly concerned $MnCl_2$ and $MnI_2$. Manganese iodide, because of its good solubility in diethyl ether, a commonly used solvent, has been much used in laboratory research. Mixed iodinated organomanganese compounds are rapidly and quantitatively prepared by the reaction of organolithium or organomanganese compounds with manganese iodide $MnI_2$ in ether. Nonetheless, the use of iodinated organomanganese compounds presents a number of drawbacks. They are prepared from manganese iodide, which is the most expensive halide and is not commercially available in a sufficiently pure form, which in some cases leads to significant decreases in yield. For industrial reasons, manganese chloride was used, which is much more economical and stable. It is nonetheless necessary to work in a solvent such as tetrahydrofuran. In fact, $MnCl_2$ is insoluble in diethyl ether and it is thus very difficult to obtain mixed chlorinated organomanganese compounds in a satisfactory manner in ether. As for $MnBr_2$, its insolubility in diethyl ether has not yet been overcome. As we will see later, it is often advantageous to use brominated organomanganese compounds in ether for organic syntheses, as yields and selectivities are better than in tetrahydrofuran. This problem (insolubility of $MnBr_2$ in ether) is surmounted by the present invention.

According to the invention, manganese bromide is complexed with lithium halides in an acyclic ether, which gives complexes soluble in diethyl ether, easily leading to the formation of brominated organomanganese solutions or suspensions in ether. The latter allow a wide variety of organic compounds to be obtained with excellent yields. In comparison to iodinated compounds, the brominated compounds obtained according to the invention have the advantage of being more economical and stable.

In comparison to chlorinated organomanganese compounds, they allow some syntheses for the preparation of these chlorinated compounds to be carried out with much better yields, whatever the solvent used: in tetrahydrofuran and in diethyl ether, in which $MnCl_2$ remains insoluble. In comparison to brominated manganese compounds in THF, they also allow better yields or better selectivities to be obtained. Acylation of RMnBr (and RMnCl) in THF gives yields which do not exceed 80% in many cases. In ether, the same reactions with RMnBr under the same conditions give yields in the order of 98%. It is also interesting to note that acylation of RmnBr (and RMnCl) in THF by mixed anhydrides (R'COOCOR'') essentially leads to the formation of esters instead of the expected ketone, whereas in ether, the same reactions with RMnBr give good yields of the ketone. Finally, the brominated compounds according to the invention make it feasible to envisage and/or carry out the preparation of certain elaborate ketones such as acetylene ketones, for example $Bu-C\equiv C-CO-CH-CH=CH-Mg$ which could not be prepared with RMnI as polymers are formed, nor with RMnCl, and particularly acetylene ketones with functional groups such as, for example $(Et_2O)_2CH-C\equiv C-CO(CH_2)_5OCHO$ and $CH_3OCH_2C\equiv C-CO-(CH_2)_5Cl$. Thus, with the brominated compounds of manganese according to the invention, it is now possible to make fine products, often fragile, by working under mild conditions, at temperatures generally ranging from $-10°$ to $+20°$ C., particularly from $0°$ to $20°$ C.

The compounds according to the invention are comprised of complexes of one molecule of $MnBr_2$ with 1 to 4 moles of a lithium halide. These are compounds generally having the formula $MnBr_2 \cdot nLiX$ wherein X is a halogen, n being 1 to 4. The especially efficacious compounds ($MnBr_4Li_2$ and $MnBr_3Li$), soluble in ether, react very quickly in ether with organolithium and organomanganese compounds to give the corresponding brominated organomanganese compounds.

The preparation of these compounds consists in mixing powdered $MnBr_2$ with an anhydrous lithium halide, in solution in an acyclic aliphatic ether, and stirring the mixture until total or partial dissolution. This operation can be carried out at room temperature.

In a variant of the invention, the $MnBr_2 \cdot nLiX$ complex can be formed in situ, at the moment a reaction using $MnBr_2$ is carried out. The lithium salt is then introduced into the medium where there is an organometal capable of reacting with $MnBr_2$, the latter being added shortly afterwards.

This is particularly the case for preparation of an organomanganese compound RMnBr, which consists in dissolving LiBr in an ethereal solution of an organomagnesium compound RMgX, then adding powdered $MnBr_2$.

In the particularly interesting case where the lithium halide is lithium bromide, it is highly advisable to use LiBr prepared directly in an acyclic aliphatic ether, for example by the reaction of bromine with lithium in this solvent, or by the reaction of an organolithium compound with an alkyl bromide or allyl bromide. It is practical to carry out these preparations in diethyl ether. They are then carried out at temperatures close to $0°$, especially from $-5°$ C. to $+5°$ C., preferably at $0°$ C. In the first example, this gives:

$$2Li + Br_2 \rightarrow 2LiBr \qquad (1)$$

In the second example, the reaction used can be:

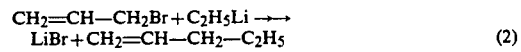

$$CH_2=CH-CH_2Br + C_2H_5Li \rightarrow LiBr + CH_2=CH-CH_2-C_2H_5 \qquad (2)$$

The lithium bromide thus obtained is soluble in ether and rapidly forms a complex of the type $MnBr_2LiBr$ when powdered $MnBr_2$ is added with stirring.

A preferred variant for facilitated preparation of the complexes according to the invention consists in using $MnBr_2$ in particles possibly exceeding $10\mu$ having a specific area of at least 3.3 m$^2$/g.

Such a salt can be prepared, in accordance with the invention, by the reaction of bromine with a metallic Mn powder in an organic liquid, particularly an aliphatic ester, preferably a $C_3$ to $C_9$ compound. Ethyl acetate, which in the same way as the majority of commonly used solvents does not dissolve the $MnBr_2$ formed can be recovered by filtration.

The samples of $MnBr_2$ obtained according to this particular characteristic of the invention had specific surfaces ranging from 3.4 to 3.9 m$^2$/g versus 3.0 in the case of commercially available manganese bromide (ALFA-INORGANIC, CHEMETALS STREM). Despite a granulometry of 5.9 to 11μ, i.e. greater than that of the commercial product (5.9μ), they dissolve more quickly in LiBr than commercially available manganese bromides.

The application of the complexes according to the invention to the synthesis of different organic compounds is carried out in an acyclic aliphatic ether, in particular in diethyl ether, ethyl-n.propyl ether, ethyl-isopropyl ether, methyl-n.propyl ether, etc. or mixtures of these compounds. It may be useful to use a co-solvent, for example a heavier acyclic ether, such as n-butyl ether.

The application of these complexes begins with the formation of a brominated organomanganese compounds by reacting an organometallic compound derived from a metal that is more electropositive than Mn with MnBr$_2$.nLiX in an acyclic aliphatic ether. Thus, in the case of a complex with LiBr, the following reaction is obtained:

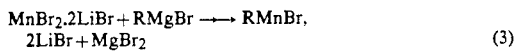

$$MnBr_2.2LiBr + RMgBr \longrightarrow RMnBr, 2LiBr + MgBr_2 \qquad (3)$$

Organomagnesium and lithium compounds are the most suitable. The reaction is carried out at a temperature ranging from −10° to +20° C., particularly from 0° to +10° C.

The presence of the Li salt exerts an unexpected stabilising effect on the organomanganese produced. In fact, it is found for example that butyl-Mn bromide in the presence of LiBr does not decompose in 2 hours at room temperature. On the other hand, in the absence of LiBr, it starts to decompose after 30 minutes at the same temperature. It follows that the brominated organomanganese compounds obtained by the reaction described hereinabove always perform better than those not derived from the complex according to the application.

The brominated organomanganese compounds derived from the MnBr$_2$.nLiX complex are suitable for a variety of known syntheses of the art, particularly with RMnI. They can thus be used for reactions such as carbonation, hydroxy-alkylation, acylation, etc., with the advantages described above.

The R group in RMnBr can be any group provided by an organolithium or organomagnesium compound, such as an alkyl, alkenyl, alkynyl, cycloalkyl, cycloalkenyl or aryl group, possibly carrying one or more substituents. The hydrocarbon part of R can include any number of carbon atoms, most often 1 to 24 carbon atoms. This is also true for the hydrocarbon groups in the compounds that can be reacted with these organomanganese compounds, in particular aldehydes, ketones, anhydrides or acid halides.

Many syntheses lead to the suprising result of the possibility of fixing more or less complicated or fragile groups, carrying different functions, onto R with good yields which could not be satisfactorily fixed when using techniques of the prior art. According to the invention, the R group of the brominated organomanganese compound can also carry functional substituents with which synthesis was difficult before now. Two examples of compounds including a triple bond, a carbonyl and an aldehyde or halogen function are given at the beginning of this description.

The following tests are given as non-limiting examples for the purpose of illustrating the invention.

EXAMPLE 1

Preparation of MnBr$_4$Li$_2$ complex in solution in ether 11.2 g (52 mmoles) of pure anhydrous MnBr$_2$ and 8.7 g (100 mmoles) of pure anhydrous LiBr are stirred with 80 ml of anhydrous ether at room temperature until a clear solution is obtained.

EXAMPLE 2

Preparation of MnBr$_3$Li complex in solution in ether

The operating procedure is the same as in example 1, except that 4.35 g (50 mmoles) of LiBr are used.

EXAMPLE 3

Preparation of LiBr 0.7 g (0.1 gram atom) of metallic Li is introduced into 80 ml of anhydrous ether and bromine is slowly added at 0° C. with stirring. The Br$_2$ rate is adjusted such that it does not exceed this temperature. The total amount of Br$_2$ introduced when the Li has totally disappeared in 8 g (50 mmoles).

EXAMPLE 4

Preparation of MnBr$_2$

The preferred operating procedure for obtaining a particularly reactive salt having a specific area greater than 3.3 m$^2$/g is as follows : 110 g of powdered metallic Mn (99% pure), i.e. 2 gram atoms, are suspended in 1500 ml of ethyl acetate with vigorous stirring. A total amount of 323 g (2.02 moles) of Br$_2$ is then added drop by drop. The reaction medium is cooled throughout the process such that the temperature does not exceed 35° C. Stirring is continued for 4 hours at 30° C.

The MnBr$_2$ precipitated is then separated by filtration on scintered glass no. 3 and washed several times with ethyl acetate. It is then placed in a heating dessicator where the remaining solvent is eliminated by progressive heating for 6 hours, up to a temperature of 200° C. under reduced pressure of 10$^{-2}$ torr. The product is then ground and dried again at 200° C. under vacuum. Yield is 95%.

EXAMPLE 5

Preparation of a brominated organomanganese compound

I.—50 mmoles of an organomagnesium compound RMgBr in solution in 80 ml of ether are mixed at 0° C. with 50 mmoles of MnBr$_4$Li$_2$ complex in solution in 80 ml of ether, prepared according to the method described in example 1. After 1 hour at +10° C., a RMnBr suspension whose color ranges from dark brown to green depending on the nature of the R group is obtained.

The process was carried out on RMnBr compounds whose R group is CH$_3$, C$_4$H$_9$—, C$_4$H$_9$—C≡C—, (CH$_3$)$_2$C═CH and (C$_2$H$_5$)$_2$CH—C≡C—, with yields of over 95%. In the case of phenyl as the R group, the mixture had to be kept at +10° C. for 4 hours.

II.—The processes carried out in par I of the example are repeated using 50 mmoles of an organolithium compound RLi instead of an organomagnesium compound. Similar results are obtained.

EXAMPLE 6

Variant on the precipitation of a brominated organomanganese compound 8.7 g (100 mmoles) of pure anhydrous LiBr are added to 80 ml of a solution containing 50 mmoles of an organomagnesium compound RMgBr in ether. After stirring for 45 minutes at room temperature, a clear solution is obtained. This solution is cooled down to $-30°$ C. and 11.2 g (52 mmoles) of powdered $MnBr_2$ are added. The solution is then stirred between 0° C. and room temperature. With most of the R groups mentioned in example 5, the organomanganese compound is generally obtained in less than an hour, with yields of 96 to 99%. In the case of phenyl, 3 hours stirring is required.

EXAMPLE 7

Comparative example with the preparation according to the examples 5 and 6

The preparations are carried out using the organomagnesium compounds in the same way as the preparations described in examples 5I and 6, but using a suspension of 50 mmoles of $MnBr_2$ without lithium salt in 80 ml of ether instead of $MnBr_4Li_2$ complex.

The mixture then has to be stirred for 8 hours instead of one hour and MnBr yield is 30 to 80%, whereas it is over 95% in the previous examples.

Moreover, the proportions are not reproducible and yield is random.

EXAMPLES 8 to 11

Application to the preparation of ketones

Various brominated organomanganese compounds RMnBr, like those prepared according to examples 5 and 6, were used to synthesize ketones. For this, 50 mmoles of acid chloride R'COCl were added to a solution or a suspension of 52 mmoles of RMnBr in 100 ml of ether at $-20°$ C. with stirring.

The temperature of the reaction medium was then adjusted to room temperature and stirring was continued for 2 hours. The medium was treated with 60 ml of 1N HCl at $-10°$ C., then adjusted to room temperature after which the decanted aqueous phase was submitted to extraction with 2 times 50 ml of ether. The combined ethereal phases were washed with 50 ml of saturated aqueous $NaHCO_3$. After drying on $MgSO_4$ and evaporation of the solvent under vacuum, the ketone formed was separated by distillation.

The table below gives ketone yields obtained from these preparations for different organic groups R and R'. These figures are the average values of the results obtained from tests carried out with RMnBr prepared according to the procedures described in examples 5I and II.

The yields obtained with RMnBr prepared according to prior art technique (example 7), i.e. without the adjunction of LiBr, are in the last vertical column (yields are more random as the reactions are not reproducible).

| Example no. | R | R' | Yields % Invention | Yields % Prior art |
| --- | --- | --- | --- | --- |
| 8 | Bu— | Bu— | 86 | 54 |
| 9 | Ph— | Bu— | 96 | 65 |
| 10 | Bu— | Hept— | 91 | 76 |
| 11 | BuC≡C— | Bu— | 88 | 41 |

It is evident that the brominated organomanganese compounds produced according to the invention give better yields than those of prior techniques. Furthermore, the results above were obtained in two hours of acylation, whereas it takes 24 hours to obtain a 77% yield of phenyl butyl ketone (Ph-CO-Bu) with the reaction Ph-MnCl+BuCOCl in ether under the conditions described hereinabove (compare with example 9).

EXAMPLE 12

Application to the preparation of a particularly fragile ketone

The organomanganese compound BuC≡C—MnBr was prepared according to the method described in example 5, then reacted with the acid chloride MeCH=CH—COCl in ether according to the operating procedure of examples 8 to 11.

The vinyl alkynyl ketone was thus obtained $$BUC\equiv C-CO-CH=CH-Me$$

with a yield of 87%, whereas starting with BuC≡C—MnI, only polymers are formed. With the corresponding chlorinated compound, yield is very low (even if THF).

What is claimed is:

1. Process for the preparation of a brominated organomanganese compound RMnBr wherein R is an organic group, by reacting an organometallic compound RM or RM'X, wherein M and M' are metals that are more electropositive than Mn and X is halogen, with $MnBr_2$ characterized in that the manganese bromide is in the form of a solution in acyclic ether of a lithium-containing complex having the composition $MnBr_2.nLiBr$, n being 1 to 4.

2. Process according to claim 1 wherein the composition of the complex is $MnBr_2.2LiBr$ or LiBr.

3. Process according to claim 1 wherein the acyclic ether is diethyl-ether, ethyl-n.propyl ether, ethyl-isopropyl ether, methyl-n. propyl ether or a mixture of such ethers.

4. Process according to claim 1 wherein the acyclic ether is a mixture of acyclic ethers having different molecular weights.

5. Process according to claim 1 wherein RM and RM'X are RLi and RMgBr respectively.

6. Process according to claim 1 wherein the solution, in acyclic ether, of the $MnBr_2.nLiBr$ complex is produced by the addition of LiBr to a dispersion, in this ether, of powdered $MnBr_2$, having a specific area of at least 3.3 m²/g.

7. Process according to claim 1, wherein it takes place at a temperature of $-10°$ C. to $+20°$ C.

8. Process according to claim 1, wherein the organic group R is an alkyl, alkenyl, or alkynyl cycloalkyl, cycloalkenyl or aryl group.

9. In the process for the preparation of an organic compound by reacting an organomanganese compound RMnBr with an organic compound carrying a functional group, the improvement which comprises stirring the functional group carrying organic compound with the acyclic ether containing RMnBr solution prepared by the process of claim 1.

10. Process according to claim 9 in which the compound carrying the functional group is an aldehyde, a ketone, a carboxylic acid halide or anhydride.

11. Process according to claim 10 to the preparation of a vinyl alkynyl ketone in which an alkynyl-MnBr is stirred with the said acyclic ether solution and then reacted with a vinyl acid chloride.

12. Process according to claim 11 in which the alkynyl-MnBr is BuC≡C—MnBr and the acid chloride is $CH_3CH=CH-COCl$.

13. A solution comprising a lithium-containing complex having the composition $MnBr_2 \cdot nLiBr$ in which n is 1 to 4, dissolved in a solvent comprising an acyclic ether.

14. A solution according to claim 13 in which said acyclic ether is at least one member of the group consisting of diethyl-ether, ethyl n-propyl ether, ethyl isopropyl ether, methyl n-propyl ether and di-n-butyl ether.

15. Solution according to claim 14 in which n is 1 or 2.

16. Solution according to claim 13 in which n is 1 or 2.

* * * * *